(12) United States Patent
Leynov et al.

(10) Patent No.: US 12,357,481 B2
(45) Date of Patent: Jul. 15, 2025

(54) IMPLANT DELIVERY DEVICES AND METHODS OF MAKING THE SAME

(71) Applicants: STRYKER CORPORATION, Kalamazoo, MI (US); STRYKER EUROPEAN OPERATIONS LIMITED, Carrigtwohill (IE)

(72) Inventors: Aleksandr Leynov, Walnut Creek, CA (US); Michael Poor, San Jose, CA (US); Hanh Ho, San Jose, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 118 days.

(21) Appl. No.: 17/182,230

(22) Filed: Feb. 22, 2021

(65) Prior Publication Data
US 2022/0265448 A1    Aug. 25, 2022

(51) Int. Cl.
*A61F 2/91*    (2013.01)
*A61B 17/00*   (2006.01)
(Continued)

(52) U.S. Cl.
CPC .............. *A61F 2/91* (2013.01); *A61F 2/9522* (2020.05); *A61F 2/966* (2013.01); *B23P 11/025* (2013.01);
(Continued)

(58) Field of Classification Search
CPC ............ A61F 2002/9505; A61F 2/9522; A61F 2002/9534; A61F 2/966; A61F 2002/9665;
(Continued)

(56) References Cited

U.S. PATENT DOCUMENTS

| 4,655,771 | A | * | 4/1987 | Wallsten | ................. D04C 1/06 606/198 |
| 5,484,444 | A | * | 1/1996 | Braunschweiler | ........ A61F 2/90 606/151 |

(Continued)

FOREIGN PATENT DOCUMENTS

| FR | 2939637 | 6/2010 |
| WO | WO 00/71058 | 11/2000 |

OTHER PUBLICATIONS

Translation of FR 2939637 A1 (Year: 2010).*

(Continued)

*Primary Examiner* — Matthew P Travers
(74) *Attorney, Agent, or Firm* — Vista IP Law Group, LLP

(57) ABSTRACT

A method of assembling an apparatus for delivering an implant to a deployment site in a patient's vasculature, includes: positioning an implant engagement member at least partially within a lumen of a tubular structure, the tubular structure having a sidewall comprising a pattern of wires or struts; heating the implant engagement member; pressing at least a portion of the sidewall of the tubular structure radially inward into a surface of the implant engagement member so that the wires or the struts of the sidewall penetrate into the surface and create corresponding recesses therein; and after the recesses are created in the surface of the implant engagement member, hardening the implant engagement member.

21 Claims, 5 Drawing Sheets

(51) Int. Cl.
*A61F 2/95* (2013.01)
*A61F 2/966* (2013.01)
*B23P 11/02* (2006.01)
*A61F 2/82* (2013.01)

(52) U.S. Cl.
CPC ............... *A61B 2017/00526* (2013.01); *A61F 2002/825* (2013.01); *A61F 2002/9534* (2013.01)

(58) Field of Classification Search
CPC ......... A61B 2017/00526; B23P 11/005; B23P 11/025
See application file for complete search history.

(56) References Cited

U.S. PATENT DOCUMENTS

| | | | | |
|---|---|---|---|---|
| 6,540,774 | B1* | 4/2003 | Cox | A61F 2/91 623/1.15 |
| 7,527,632 | B2* | 5/2009 | Houghton | A61F 2/958 623/1.11 |
| 2004/0106977 | A1* | 6/2004 | Sullivan | A61F 2/95 623/1.12 |
| 2007/0199360 | A1* | 8/2007 | Sarac | A61F 2/95 264/319 |
| 2007/0293930 | A1* | 12/2007 | Wang | A61F 2/966 623/1.11 |
| 2010/0292778 | A1* | 11/2010 | Roeder | A61F 2/91 623/1.17 |
| 2014/0172067 | A1 | 6/2014 | Brown et al. | |
| 2014/0222128 | A1 | 8/2014 | Dusbabek et al. | |
| 2014/0350657 | A1* | 11/2014 | Headley | A61F 2/91 623/1.15 |
| 2017/0367856 | A1* | 12/2017 | Tanaka | A61F 2/86 |

OTHER PUBLICATIONS

PCT International Search Report and Written Opinion for International Appln. No. PCT/US2022/015867, Applicant Stryker Corporation, dated Apr. 29, 2022 (10 pages).

* cited by examiner

IMPLANT DELIVERY DEVICES AND METHODS OF MAKING THE SAME

FIELD

The field of the disclosure relates to medical devices, and more specifically, to delivery devices, such as delivery catheters, for delivering implants, and methods of making the same.

BACKGROUND

Various implants may be delivered inside patients for treatment and/or diagnostic purposes. One type of implant is stent, which is configured to be delivered inside a vasculature of a patient.

In order to deliver the stent, a pusher located inside the delivery tube may be utilized to advance the stent distally relative to the delivery tube. The pusher will need to be able to advance the stent with a force that overcomes the frictional force between the stent and an inner surface of a wall of the delivery tube. In some cases, if the coupling force between the pusher and the stent is too great, the stent may "stuck" with the pusher temporarily after the stent is deployed out of the delivery tube, and the stent may not efficiently and immediately decouple from the pusher.

New delivery devices and techniques for delivering implants, such as stents, and new way of making such delivery devices, are described herein.

SUMMARY

A method of assembling an apparatus for delivering an implant to a deployment site in a patient's vasculature, includes: positioning an implant engagement member at least partially within a lumen of a tubular structure, the tubular structure having a sidewall comprising a pattern of wires or struts; heating the implant engagement member; pressing at least a portion of the sidewall of the tubular structure radially inward into a surface of the implant engagement member so that the wires or the struts of the sidewall penetrate into the surface and create corresponding recesses therein; and after the recesses are created in the surface of the implant engagement member, hardening the implant engagement member.

Optionally, the implant engagement member is positioned within the lumen of a tubular structure prior to heating the implant engagement member.

Optionally, the implant engagement member is attached to a distal end portion of an elongated core member prior to being positioned within the lumen of the tubular structure.

Optionally, the wires or the struts of the tubular structure are pressed into the surface of the implant engagement member by axially stretching the tubular structure.

Optionally, the implant engagement member is hardened while the wires or struts of the tubular structure remain at least partially seated in the recesses formed in the surface of the implant engagement member.

Optionally, the recesses formed in the surface of the implant engaging member comprise a substantially mirror image of the pattern of wires or struts of the at least a portion of the tubular structure.

Optionally, the implant engagement member is hardened to a hardness that is at least 25 A.

Optionally, the tubular structure is the implant, and wherein the wires or the struts comprise braided wires.

Optionally, the tubular structure is the implant, and wherein the wires or the struts comprise struts formed by laser-cutting a tube.

Optionally, the tubular structure is a separate structure from the implant, and wherein the pattern of the wires or the struts is substantially identical to a pattern of wires or struts of the implant.

Optionally, the method further includes separating the tubular structure from the implant engagement member prior to hardening the implant engagement member.

Optionally, the method further includes separating the tubular structure from the implant engagement member, and positing at least a portion of the implant onto the implant engagement member such that the wires or the struts of the at least a portion of the implant are seated in respective recesses formed in the surface of the implant engagement member.

Optionally, the implant engagement member is heated using a sterilization heat source.

Optionally, at least one of the recesses comprises a groove forming a non-zero degree angle with respect to an imaginary line that is parallel to a longitudinal axis of the implant engagement member.

Optionally, the act of heating is performed before the act of pressing.

Optionally, the act of heating is performed after the act of pressing.

Optionally, the method further includes placing the implant engagement member and the tubular structure in an introducer sheath to form at least a part of a product, and wherein the act of heating is performed on the at least a part of the product.

A system for delivering an implant to a deployment site within a patient's vasculature, the tubular implant having a sidewall comprising a pattern of wires or struts, includes: an elongated core member; and an implant engagement member coupled to a distal end portion of the elongated core member, the implant engagement member comprising a surface having a plurality of recesses formed therein that receive and accommodate the wires or the struts of a corresponding sidewall portion of the tubular implant, wherein the recesses formed in the surface of the implant engagement member comprise a substantially mirror image of the pattern of the wires or the struts of the corresponding sidewall portion of the tubular implant.

Optionally, the wires or the struts of the tubular implant comprise braided wires.

Optionally, the wires or the struts of the tubular implant comprise struts formed by laser-cutting a tube.

Optionally, the implant engagement member has a hardness that is at least 25 A.

Optionally, the system further includes an additional recess in the surface of the implant engagement member configured to accommodate at least a portion of a marker of the tubular implant.

Optionally, the system further includes a delivery catheter; wherein the elongated core member, the implant engagement member, and the tubular implant are at least partially disposed within a lumen of, and slidable relative to, the delivery catheter; wherein the implant engagement member and the delivery catheter are configured to cooperate with each other to grip the tubular implant as the elongated core member is moved through and within the lumen of the delivery catheter; and wherein the tubular implant is configured to change from a compressed delivery configuration to an expanded deployed configuration with an expansion force that is sufficiently larger than a frictional force exerted by the recesses on the wires or the struts of the implant engagement member once the tubular implant is no longer confined within the delivery catheter.

Other and further aspects and features will be evident from reading the following detailed description.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
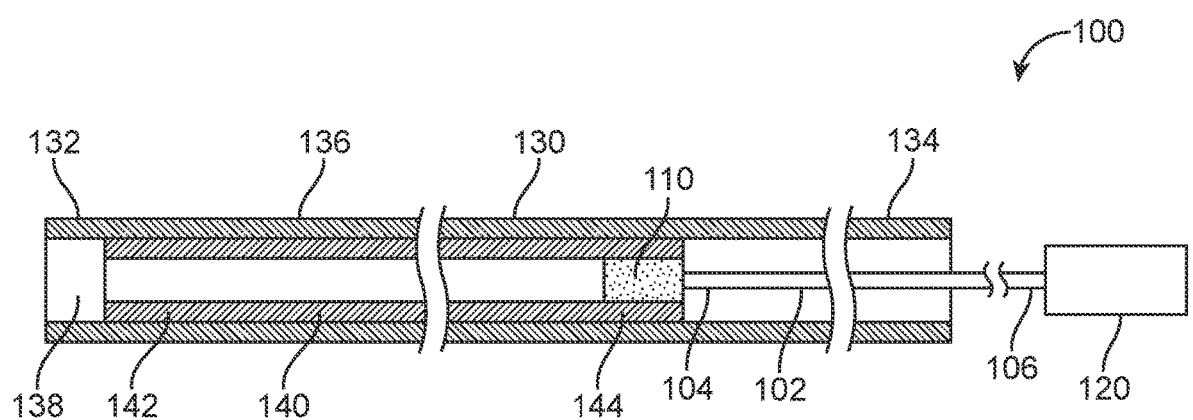
FIG. 1 illustrates a medical device configured to deliver an implant in accordance with some embodiments.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a medical device 100 configured to deliver an implant in accordance with some embodiments. The medical device 100 includes an elongated structure (e.g., an elongated core member) 102 having a distal end 104 and a proximal end 106, an implant engagement member 110 coupled to a distal end 104 (e.g., a distal end portion) of the elongated structure, and a handle 120 coupled to the proximal end 106 of the elongated structure 102. The medical device 100 also includes a sheath 130 having a sheath distal end 132, a sheath proximal end 134, and a sheath body 136 extending between the sheath distal end 132 and the sheath proximal end 134. The sheath 130 has a lumen 138 for housing an implant 140 to be delivered into a patient.

In some embodiments, the sheath 130 may be a part of a catheter (e.g., a microcatheter). In other embodiments, the sheath 130 may be a tubing configured to package and contain the implant 140. In such cases, during a medical procedure, the implant 140 together with the implant engagement member 110 and the elongated structure 102 may be transferred from the sheath 130 into a catheter (e.g., microcatheter) after the catheter's distal tip has been placed at a desired location inside a patient. After advancement through the catheter, the implant 140 will be deployed out of a distal end of the catheter.

As shown in FIG. 1, the implant engagement member 110 is disposed in the lumen 138 of the sheath 130, and is moveable (e.g., translatable) relative to the sheath 130 along a longitudinal axis of the elongated member 102 in response to movement of the handle 120 relative to the sheath 130. Alternatively or additionally, the sheath 130 may be moved (e.g., translated) relative to the handle 120 to create the relative movement between the implant engagement member 110 and the sheath 130.

The implant engagement member 110 and the sheath 130 are configured to cooperate with each other to grip and to release the implant 140. In particular, as shown in FIG. 1, while the implant 140 is being housed in the lumen 138 of the sheath 130, the proximal end 144 of the implant 140 is engaged with the implant engagement member 110, and is being "gripped" between the implant engagement member 110 and an inner surface of a wall of the sheath 130.

As shown in the figure, the implant engagement member 110 is configured to engage with an inner surface of the implant 140 when the implant 140 is housed within the sheath 130. In the illustrated embodiments, the implant engagement member 110 comprises a surface, and a plurality of grooves (e.g., grooves 502 shown in FIGS. 4-5) at the surface of the implant engagement member 110, wherein the grooves form a pattern that matches at least a part of a braid pattern of the implant 140. This feature is advantageous because it allows the proximal end 144 of the implant 140 to be in mating engagement with the grooves at the surface of the implant engagement member 110. As a result, the proximal end 144 of the implant 140 is detachably anchored to the implant engagement member 110 via the grooves at the surface of the implant engagement member 110. In some embodiments, the implant 140 may include braids forming a braid pattern. In such cases, the grooves at the surface of the implant engagement member 110 form a pattern that matches the braid pattern of the implant 140. This allows at least parts of some of the braids (e.g., the parts of the braids at the proximal end 144) of the implant 140 to be accommodated in the respective grooves of the implant engagement member 110. The grooves of the implant engagement member 110 will be described in further details below.

Figure 2:
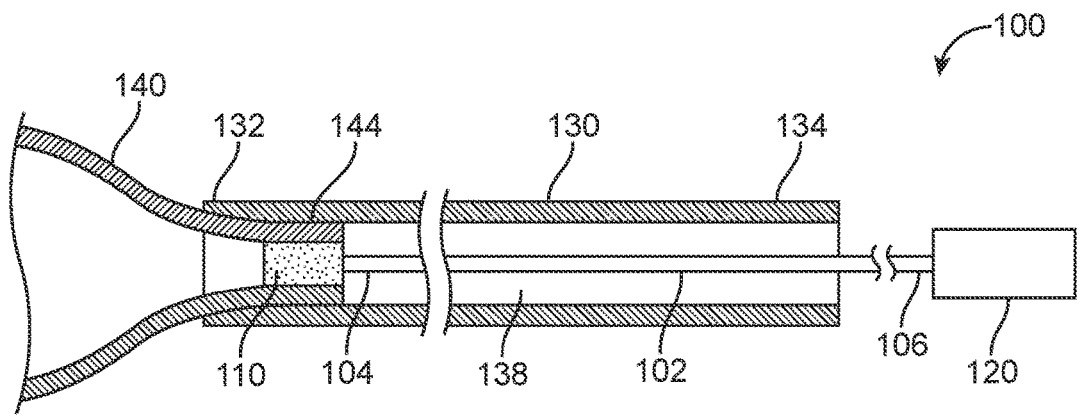
FIG. 2 illustrates the medical device of FIG. 1, particularly showing a part of the implant being delivered out of the catheter.

As shown in FIG. 2, after the sheath distal end 132 of the sheath 130 has been desirably placed inside the patient at a target location, at least a part (e.g., the distal end 142—shown in FIG. 1) of the implant 140 may be deployed out of the sheath 130. Such may be accomplished by moving the handle 120 distally relative to the sheath 130, and/or moving the sheath 130 proximally relative to the handle 120. The distal movement of the handle 120 and/or the proximal movement of the sheath 130 causes the implant engagement member 110 to move towards the distal end 132 of the sheath 130. As the implant engagement member 110 moves distally relative to the sheath 130, the implant engagement member 110 carries the implant 140 with it, thereby causing the implant 140 to move distally relative to the sheath 130. The carrying of the implant 140 by the implant engagement member 110 is due to the fact that some of the implant components (e.g., braids) of the implant 140 are at least partially disposed within respective grooves (e.g., the grooves 502 shown in FIGS. 4-5) of the implant engagement member 110. As part of the implant 140 is being deployed out of the lumen 138 of the sheath 130, the part of the implant 140 transitions from its delivery configuration to a deployed configuration, like that shown in FIG. 2.

The delivery configuration of the implant 140 (or a part of the implant 140) has a cross-sectional dimension that is less than a cross-sectional dimension of the deployed configuration of the implant 140 (or the part of the implant 140). For example, as shown in FIG. 2, the majority of the implant 140 has been deployed outside the sheath 130 while the proximal end 144 of the implant 140 remains inside the lumen 138 of the sheath 130. The proximal end 144 is gripped between the sheath 130 and the implant engagement member 110, and has its delivery configuration while being inside the sheath 130. The cross-sectional dimension of the proximal end 144 of the implant 140 in its delivery configuration inside the lumen 138 of the sheath 130, is less than the cross-sectional dimension of the other part(s) of the implant 140 that has been delivered outside the lumen 138 of the sheath 130.

In some cases, if the physician desires to reposition the partially deployed implant 140, and/or to adjust a configuration of the deployed implant 140, the physician may move the handle 120 proximally relative to the sheath 130. This results in the implant engagement member 110 moving proximally relative to the sheath 130. Since the proximal end 144 of the implant 140 is in mating engagement with the grooves at the surface of the implant engagement member 110, the proximal end 144 of the implant 140 is anchored to the implant engagement member 110 via the grooves at the surface of the implant engagement member 110. As a result, proximal movement of the implant engagement member 110 relative to the sheath 130 will cause the deployed part of the implant 140 to be pulled back into the lumen 138 of the sheath 130, resulting in the part of the implant 140 assuming the delivery configuration inside the sheath 130. In some cases, all of the previously deployed part(s) of the implant 140 may be retrieved back into the lumen 138 of the sheath 130. The physician may then reposition the sheath 130 to place the distal end 132 of the sheath 130 in a different position for re-deployment of a part of the implant 140.

Figure 3:
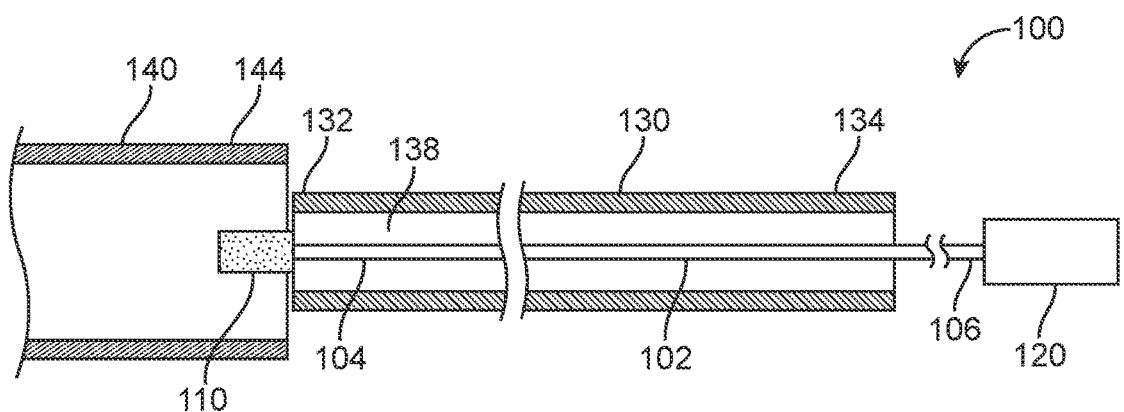
FIG. 3 illustrates the medical device of FIG. 1, particularly showing entirety of the implant having been delivered out of the catheter.

In some cases, the entirety of the implant 140 may be deployed out of the lumen 138 of the sheath 130. FIG. 3 illustrates the medical device of FIG. 1, particularly showing an entirety of the implant 140 having been delivered out of the sheath 130. As shown in FIG. 3, as soon as the proximal end 144 of the implant 140 is pushed out of the lumen 138 of the sheath 130 by the implant engagement member 110, the proximal end 144 of the implant 140 springs radially outward to transition from its delivery configuration to a deployed configuration. When in the deployed configuration the implant 140 has a cross-sectional dimension that is larger than that when the implant 140 is in the delivery configuration.

Figure 4A:
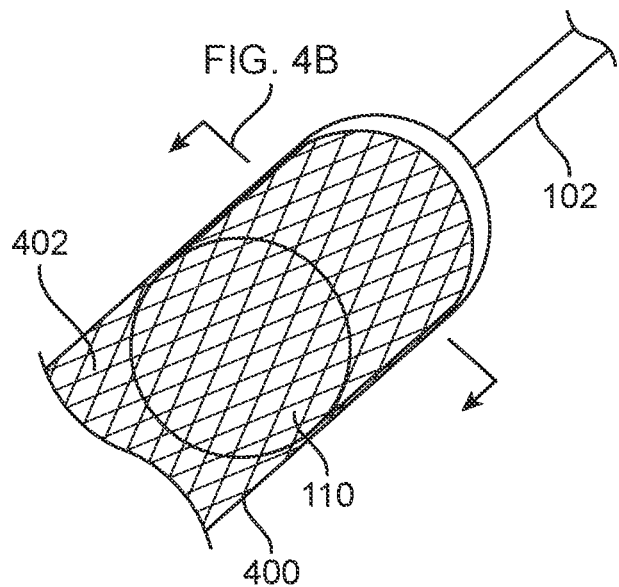
FIG. 4A illustrates an implant engagement member engaging with an implant in accordance with some embodiments.
Figure 4B:
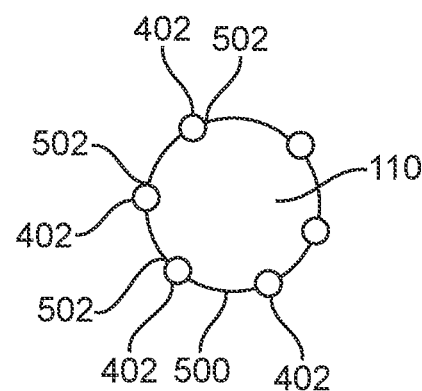
FIG. 4B illustrates a cross-sectional view of the implant engagement member with the implant of FIG. 4A.

FIG. 4A shows the implant engagement member 110 engaging an implant 400. The implant 400 may be an example of the implant 140 of FIG. 1. In FIG. 4A, the sheath 130 is not shown for clarity purpose. As shown in the figure, the implant has a plurality of implant components 402. In the illustrated embodiments, the implant is a braided implant, and the implant components 402 are braid elements (e.g., filaments, wires, strands, fibers, etc.). In other embodiments, the implant 400 may be other types of implant, and the implant components 402 may be other types of component for an implant. In the illustrated example shown, the implant 400 is in the delivery configuration while being engaged with the implant engagement member 110 and while being housed inside the sheath 130 (not shown). FIG. 4B shows a cross-section of the implant engagement member 110 in engagement with the implant 400. The implant engagement member 110 comprises a surface 500 having a plurality of grooves 502. The grooves 502 are configured to accommodate respective implant components 402 (e.g., braid elements) of the implant 400. In the illustrated embodiments, the grooves 502 form a pattern that matches at least a part of a pattern of the implant components 402 (e.g., braid pattern) of the implant 140.

As shown in FIG. 4B, the implant 140 comprises a tubular structure (formed by the implant components 402) with an external cross-sectional dimension. A cross-sectional dimension of the implant engagement member 110 is less than the external cross-sectional dimension of the tubular structure of the implant 140. The tubular structure of the implant 140 (formed by the implant components 402) also has an internal cross-sectional dimension. Because the implant components 402 sit at least partially within the grooves 502 of the engagement member 110, the internal cross-sectional dimension of the tubular structure of the implant 140 (i.e., when the implant 140 is circumferentially engaged with the implant engagement member 110) is less than the largest cross-sectional dimension of the implant engagement member 110.

Also, as shown in FIG. 4B, the implant components 402 is disposed partially in the respective grooves 502 of the implant engagement member 110. In some embodiments, the depth of each groove 502 is at least 5% of a maximum thickness of the implant component 402. For example, if the implant 140 has a braid element (e.g., a single braid fiber or a group of braid fibers forming into an elongated member), the depth of each groove 502 is at least 5% of the thickness of the braid element of the implant. In other embodiments, the depth of each groove 502 may be at least 10%, at least 15%, at least 20%, at least 25%, at least 30%, at least 40%, at least 50%, at least 60%, at least 70%, at least 80%, at least 90% (e.g., 100%) of the thickness of the implant component 402.

In addition, in some embodiments, a width (measured in a direction that is perpendicular to a longitudinal axis) of the groove 502 may be less than a width of an implant component (e.g., a braid element). In other embodiments, the width of the groove 502 may be the same as the width of the implant component. In further embodiments, the width of the groove 502 may be more than the width of the implant component.

Figure 5A:
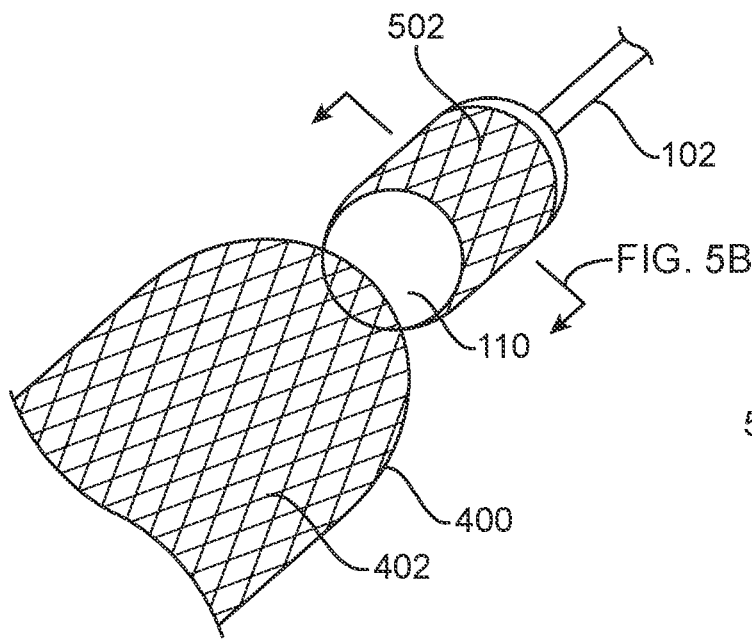
FIG. 5A illustrates the implant of FIG. 4A, particularly showing the implant being disengaged from the implant engagement member.
Figure 5B:
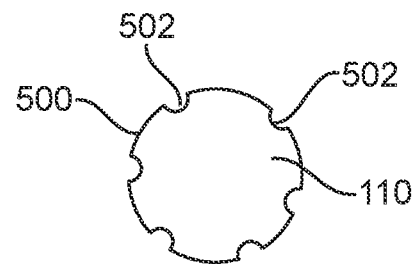
FIG. 5B illustrates a cross-sectional view of the implant engagement member of FIG. 5A.

FIG. 5A illustrates the implant 400 of FIG. 4A, particularly showing the implant 400 being disengaged from the implant engagement member 110. This happens when the implant engagement member 110 coupling to the implant 400 exits the lumen 138 of the sheath 130. As a result, the implant 400 is no longer gripped between the sheath 130 and the implant engagement member 110. As shown in the figure, because the implant 400 has expanded into its deployed configuration, the implant components 402 form a pattern that no longer matches the pattern of the grooves 502 at the surface 500 of the implant engagement member 110. FIG. 5B illustrates a cross-sectional view of the implant engagement member 110 of FIG. 5A, particularly showing the grooves 502 without the respective implant components 402 disposed therein.

In the illustrated embodiments, the implant engagement member 110 is made from a material that provides sufficient hardness for the implant engagement member 110, so that the implant components 402 (e.g., the braid elements) of the implant 400 will not "stick" to grooves 502 of the implant engagement member 110 to temporarily prevent the proximal end 144 of the implant 400 from disengaging from the implant engagement member 110. For example, in some embodiments, the implant engagement member 110 may have a hardness that is at least 25 A, at least 30 A, at least 40 A, at least 50 A, at least 60 A, at least 70 A, at least 80 A, or higher.

In some embodiments, the implant 140 is configured to change from the delivery configuration to the deployed configuration with an expansion force that is larger than a frictional force exerted by the grooves 502 of the implant engagement member 110 on the implant 140. The expansion force may be larger than the gripping force by a sufficient amount that allows the proximal end 144 of the implant 140 to immediately spring open to assume the deployed configuration when the proximal end 144 of the implant 140 is unconfined by the sheath 130. In one implementation, the implant engagement member 110 may be made from a deformable and pliable material, which allows the surface of the implant engagement member 110 to be indented by a tool pressing against it. The tool may have a pattern of the grooves to be formed on the surface of the implant engagement member 110. After the surface of the implant engagement member 110 has been indented to form the grooves, the implant engagement member 110 may be temperature-treated to permanently set the indentations (grooves). For example, the implant engagement member 110 may be initially heated to soften the implant engagement member 110, thereby allowing the grooves to be more easily formed. In some embodiments, a sterilization heat source may be utilized to apply heat for sterilizing the implant engagement member 110 and/or the implant 140. In such cases, the heat for sterilization may be used to soften the implant engagement member 110 during the sterilization process. In other embodiments, a separate heat source may be utilized to heat the implant engagement member 110. After the grooves are formed, the implant engagement member 110 may be cooled to harden the implant engagement member 110 with the grooves. In other embodiments, instead of or in addition to being temperature-treated, the implant engagement member 110 may be chemically-treated, laser-treated, optically-treated, or may be simply cured by letting time passed, in order to set the indentations to form the permanent grooves. In some embodiments, the implant engagement member 110 may be made from a polymer, such as a thermal plastic polymer. In other embodiments, the implant engagement member 110 may be made from other materials. As used in this specification, the term "permanently set" or any of other similar terms refers to any action that causes the indentations/grooves to take on a form or characteristic that is more permanent (e.g., such as making the object with the indentations/grooves harder) that that before the action is performed. Similarly, the term "permanent grooves" refer to grooves that has a more permanent form compared to that before the object with the grooves is made harder.

Also, in other embodiments, the implant engagement member 110 may be 3D-printed with permanent grooves by design. The groove pattern for the 3D printing file may be obtained by scanning (e.g., high-resolution 3D scanning) of a previously formed engagement member. For example, the previously formed engagement member may be formed by indenting a surface of the implant engagement member 110 and by temperature treatment, as discussed herein.

In the illustrated embodiments, at least one of the grooves 502 form an angle that is larger than 0 degree with respect to an imaginary line that is parallel to a longitudinal axis of the elongated structure 102. In other embodiments, one of the grooves 502 may form a first angle with respect to an imaginary line that is parallel to the longitudinal axis of the elongated structure 102, and another one of the grooves may form a second angle with respect to an imaginary line that is parallel to the longitudinal axis of the elongated structure 102. The first angle and the second angle may be the same. Alternatively, the first angle and the second angle may be different from each other. Also, in some embodiments, the pattern of the grooves 502 of the implant engagement member 110 may comprise a crisscross pattern. In other embodiments, the grooves 502 at the surface 500 of the implant engagement member 110 may form other patterns, such as a spiral pattern, a grid pattern, a zig-zag pattern, a user-defined pattern, a symmetric pattern, an asymmetric pattern, etc.

It should be noted that providing the implant engagement member 110 with grooves 502 (wherein at least one of the grooves 502 form an angle that is larger than 0 degree with respect to an imaginary line parallel to the longitudinal axis of the elongated structure 102) is advantageous, because it allows the implant engagement member 110 to more efficiently move the proximal end 144 of the implant 140 distally or proximally relative to the sheath 130. This is because if all of the grooves 502 are parallel to the longitudinal axis of the elongated structure 102, and if all of the implant components are also parallel to the longitudinal axis, then the axial force applied in a direction of the longitudinal axis of the elongated structure 102 will be parallel to the extension of the grooves 502. In such cases, in order for the proximal end 144 of the implant 140 to be moved by the implant engagement member 110, the device 100 will need to rely on all frictional forces between the implant components of the implant 140 and the implant engagement member 110. On the other hand, if at least one of the grooves 502 and at least a corresponding one of the implant components are not parallel to the longitudinal axis of the elongated structure 102, then the axis force applied in the direction of the longitudinal axis of the elongated structure 102 will have at least some force component that "pushes" against the implant component, resulting in a more efficient way of moving the implant 140 (and with less frictional force between the implant 140 and the implant engagement member 110).

In some embodiments, the implant 140 may be a stent configured to be delivered inside a vasculature of a patient. In other embodiments, the implant 140 may be a vaso-occlusive device configured for placement inside an aneurysm. In such cases, in addition to the implant 140 springing open radially from its longitudinal axis upon deployment of the implant 140, the implant 140 also elastically assumes a three-dimensional configuration (e.g., by bending or flexure action). For example, in some embodiments, the implant 140 may be a braided tubular elongated member having a profile that follows the curvature of the sheath 130 when contained inside the sheath 130. After the implant 140 is deployed out of the sheath 130, the braided tubular elongated member expands radially away from the longitudinal axis of the braided tubular elongated member, and the braided tubular elongated member also bends to form a series of loops (e.g., open loops, and/or closed loops) to assume a relaxed three-dimensional configuration. The relaxed three-dimensional configuration formed by the implant 140 is configured to at least partially fill a space inside an aneurysm. In further embodiments, the implant 140 may be other types of implant.

As used in this specification, the term "relaxed three-dimensional configuration" of an implant refers to the three-dimensional configuration of the implant when the implant is not confined within a delivery tube (e.g., the sheath 130). For example, the relaxed three-dimensional configuration of the implant may be the configuration of the implant when the implant is delivered inside the patient, or when the implant is resting freely on a surface outside the patient.

Figure 6A:
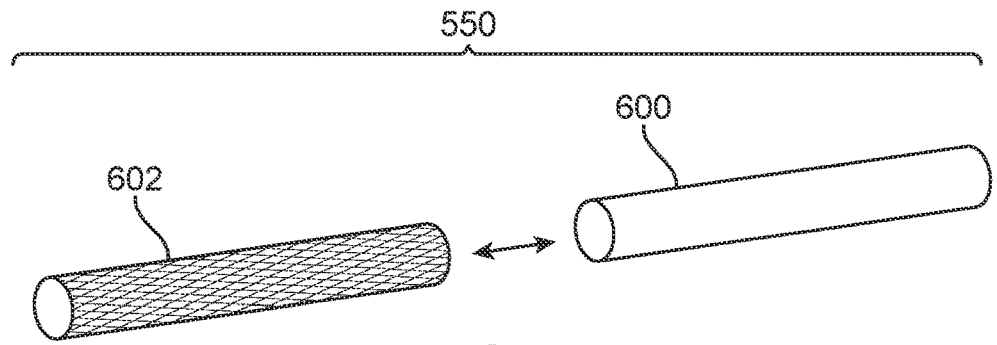
FIGS. 6A-6D illustrate a system and a technique for making a medical device in accordance with some embodiments.
Figure 6B:
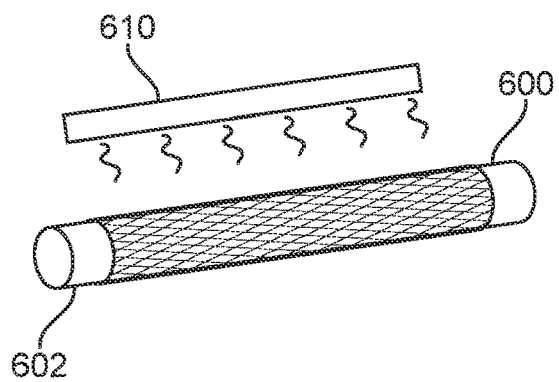

FIGS. 6A-6D illustrate a system 550 and a technique for making a medical device in accordance with some embodiments. The system 550 includes an object 600 to be formed as the implant engagement member 110. The system 550 also includes a tubular structure 602 with a braid pattern. In some embodiments, the tubular structure 602 may have the same characteristics as an implant (e.g., the implant 140), or the tubular structure 602 may be an implant itself. In the illustrated embodiments, the tubular structure 602 may be a braided tubular structure made from a plurality of braid elements. To make the implant engagement member 110 with the grooves 502, the object 600 without the grooves 502 is first placed inside the lumen of the tubular structure 602 (FIG. 6A). The tubular structure 602 may be stretched to make it collapse radially inward to engage with the object 600 (FIG. 6B). Alternatively or additionally, the tubular structure 602 may be inserted into a sheath (e.g., the sheath 130). The inner wall of the sheath applies a force towards the tubular structure 602 to press it inwardly to engage with the object 600. The object 600 may have a soft and/or deformable characteristic that allows the components (e.g., braid elements) of the tubular structure 602 to indent the surface of the object 600. After the indentations on the surface of the object 600 are made, the object 600 may be temperature treated (e.g., by a cooling source 610) to permanently set the indentations, forming grooves at the surface of the object 600. Alternatively or additionally, the object 600 may be chemically-treated by one or more chemicals, laser-treated by a laser device, or may be simply cured by passage of time, to set the grooves at the surface of the object 600.

In other embodiments, the object 600 may initially have a relatively hard characteristic. The object 600 may be placed on a mandrel for support by the mandrel. The tubular structure 602 is then placed over the object 600. The tubular structure 602 may be stretched and/or compressed to urge the tubular structure 602 towards the object 600. Alternatively or additionally, a tube (e.g., a heat shrink tubing) may be placed over the tubular structure 602 to push the tubular structure 602 towards the object 600. As heat is applied to the object 600, the object 600 becomes softer (hardness decreases), thereby allowing the structural components of the tubular structure 602 to more easily indent the surface of the object 600. After the indentations (grooves) are created, the object 600 is then cooled to set grooves.

Figure 6C:
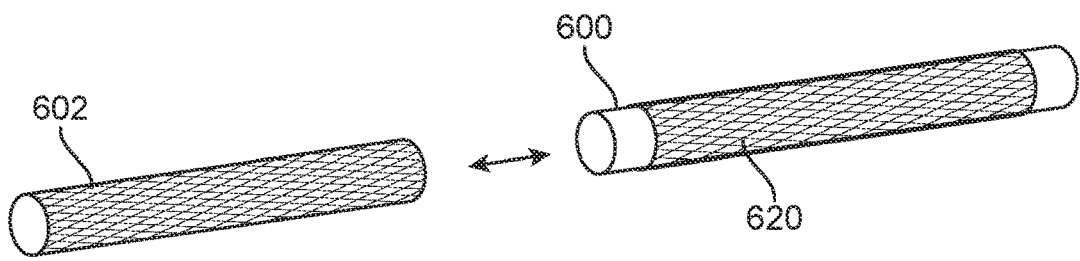
Figure 6D:
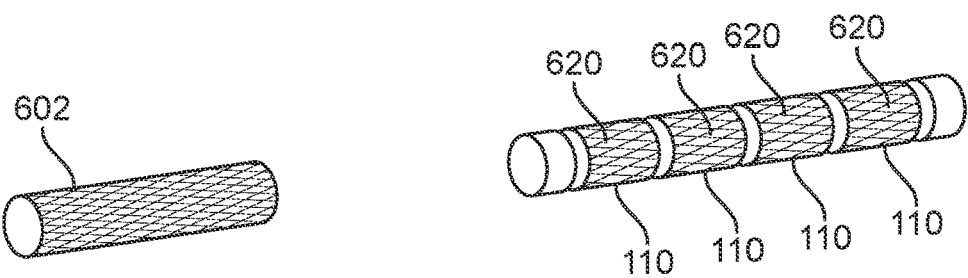

Next, the tubular structure 602 is removed from the object 600 (FIG. 6C). As shown in the figure, the object 600 now has grooves 620 formed at the surface of the object 600. The grooves 620 have a pattern that matches the braid pattern of the tubular structure 602. Next, the object 600 with the grooves 620 are then cut (e.g., by a mechanical cutter, laser cutter, etc.) into pieces of engagement members 110 (FIG. 6D).

In the above embodiments, the object 600 has an elongated configuration, which allows grooves to be formed on multiple engagement members 110 simultaneously. In other embodiments, the object 600 may have a shorter configuration. For example, in other embodiments, the object 600 may have a length sufficient for forming only one engagement member 110.

Also, in the above embodiments, the tubular structure 602 used to form the grooves 620 on the object 600 is not the implant that is to be delivered by any of the formed engagement members 110. Rather, the tubular structure 602 is used only during the manufacturing process to create the grooves 620 on the object 600. In one implementation, the tubular structure 602 may be an implant that is originally produced for implantation purpose, but is then used instead in a manufacturing process to create the grooves on the implant engagement member 110. In such cases, the tubular structure 602 has identical features as those of the implant. In other embodiments, the tubular structure 602 may not be identical to an implant, but may have certain characteristics that are the same as those of the implant. For example, in other embodiments, the tubular structure 602 may have a braid pattern or surface texture that is the same as that of the implant (when the implant is it is collapsed or delivery configuration in abutment with the implant engagement member 110 to be formed).

In other embodiments, the tubular structure 602 being used to form the grooves 620 on the object 600 may be the implant that is to be coupled to the implant engagement member 110 being formed. In one implementation, the tubular structure 602 (which is the implant 140 in this example) is placed over the object 600. The object 600 is configured to form one engagement member 110 in this example, and therefore has a length that corresponds with a length of the implant engagement member 110 to be formed. The implant 140 may be stretched to make it collapse radially inward to engage with the object 600. Alternatively or additionally, the implant 140 may be inserted into a sheath (e.g., the sheath 130) to cause the implant 140 to assume its delivery configuration and to push the proximal end 144 of the implant 140 radially inward to engage with the object 600. The object 600 may have a soft and/or deformable characteristic that allows the implant components (e.g., braid elements) of the implant 140 to indent the surface of the object 600. Alternatively, the object 600 may be heated to soften the object 600 to allow the indentations to be made on the surface of the object 600. In some embodiments, the object 600 and/or the implant 140 may be sterilized using a heat source that applies heat to the object 600 and/or the implant 140. In such cases, the heat from the sterilization process may be utilized to soften the object 600 for creating the indentations on the surface of the object 600. Also, in some embodiments, the heating of the object 600 may be performed in the finished-good configuration, in which the implant 140 is coupled to the object 600 (engagement member) and is inside an introducer sheath. Alternatively, instead of using sterilization heat source, a separate heat source may be utilized to apply heat on the object 600. After the indentations on the surface of the object 600 are made, the object 600 may be treated to permanently set the indentations, forming the grooves at the surface of the object 600 (which becomes the implant engagement member 110).

It should be noted that in order to create a pattern of grooves 502 at the surface of the implant engagement member 110 so that the pattern matches the pattern of the implant components 402 (e.g., braid elements) of the implant 400, the pattern of the indenting elements (for creating the indentations at the object 600) at the tubular structure 602 must be the same as the pattern of the implant components 402 of the implant 400 when the implant 400 is in its collapsed (delivery) delivery configuration (e.g., when collapsed to engage with the implant engagement member 110).

In the embodiment depicted in FIG. 6, the tubular structure 602 has a grid-pattern. In other embodiments, the tubular structure 602 may have other configurations. For example, in other embodiments, the structure 602 may have a spiral pattern, a grid pattern, a zig-zag pattern, a user-defined pattern, a symmetric pattern, an asymmetric pattern, etc. In some embodiments, any of such patterns may correspond with at least a part of the pattern formed by the implant components 402 of the implant 400.

Figure 7:
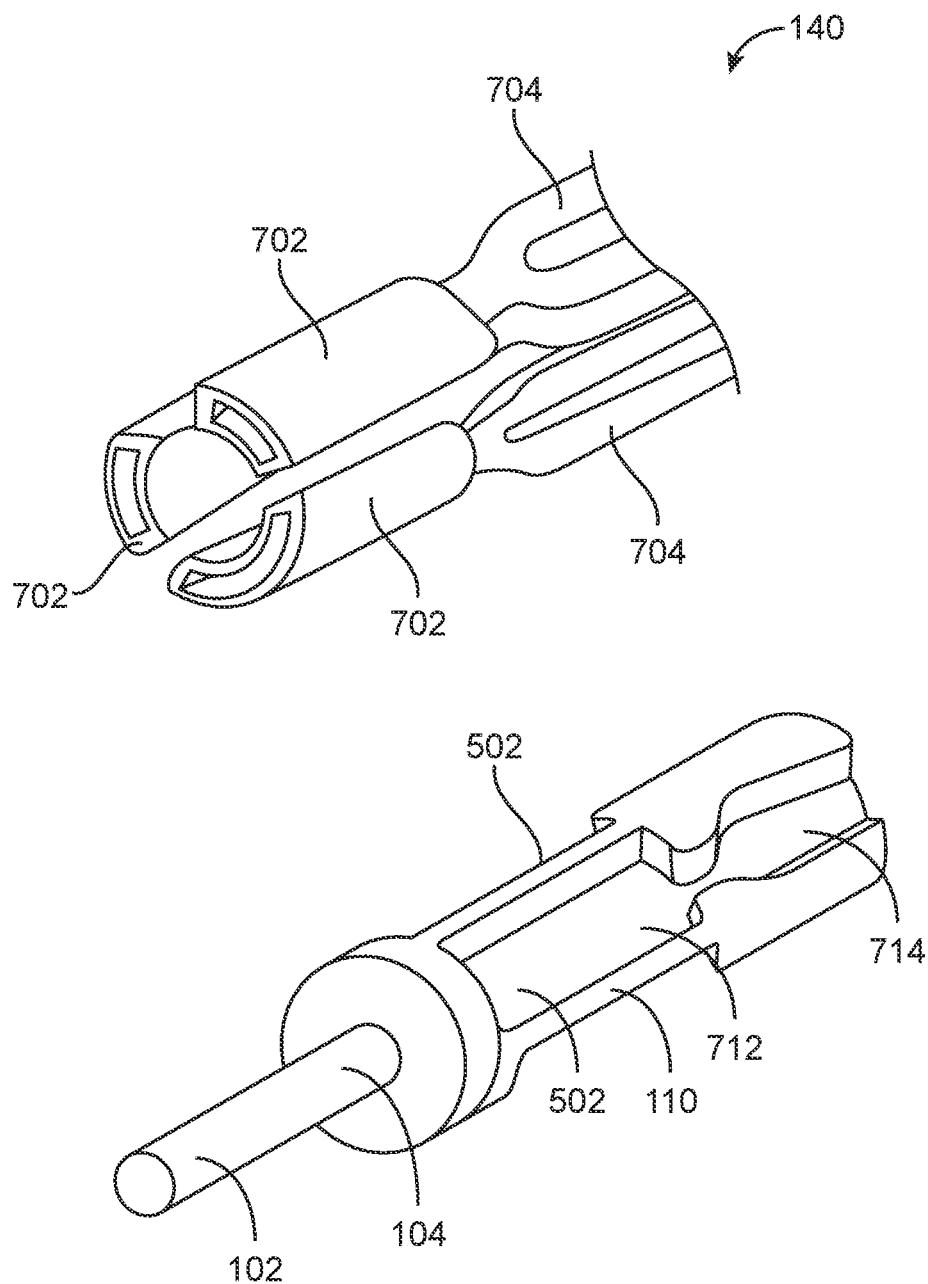
FIG. 7 illustrates an implant engagement member of a medical device and a corresponding implant in accordance with other embodiments.

Also, in the above embodiments, the implant engagement member 110 is described as having grooves. However, the features at the implant engagement member 110 are not limited to grooves. In other embodiments, the implant engagement member 110 may have any indentations or depressions, wherein the indentations or depressions may have any sizes and/or shapes. FIG. 7 illustrates another example of an implant engagement member 110, and a corresponding implant 140 in accordance with other embodiments. As shown in the figure, the implant 140 is a stent having a plurality of markers 702 at one end and a plurality of struts 704 extending from the body of the stent and connecting with the markers 702. The implant engagement member 110 has recesses (e.g., indentations or depressions) 502 that are configured to receive respective components of the implant 140. The recesses 502 have respective geometries (e.g., size, shape, position, or any combination of the foregoing) that correspond with the respective components of the implant. The recesses 502 includes indentations 712 configured to receive the respective markers 702 of the implant 140, and indentations 714 configured to receive the respective struts 704 of the implant 140. As shown in the figure, the indentation 712 has a shape and size that correspond with the shape and size of the marker 702. Similarly, the indentation 714 has a shape and size that correspond with the shape and size of the strut 704. Also, the indentations 712, 714 form a pattern that matches the pattern of the markers and the structs 704. This allows the implant engagement member 110 to receive the implant 140 in a mating configuration. It should be noted that groove, indentation, and depression are all examples of a "recess".

Figure 8:
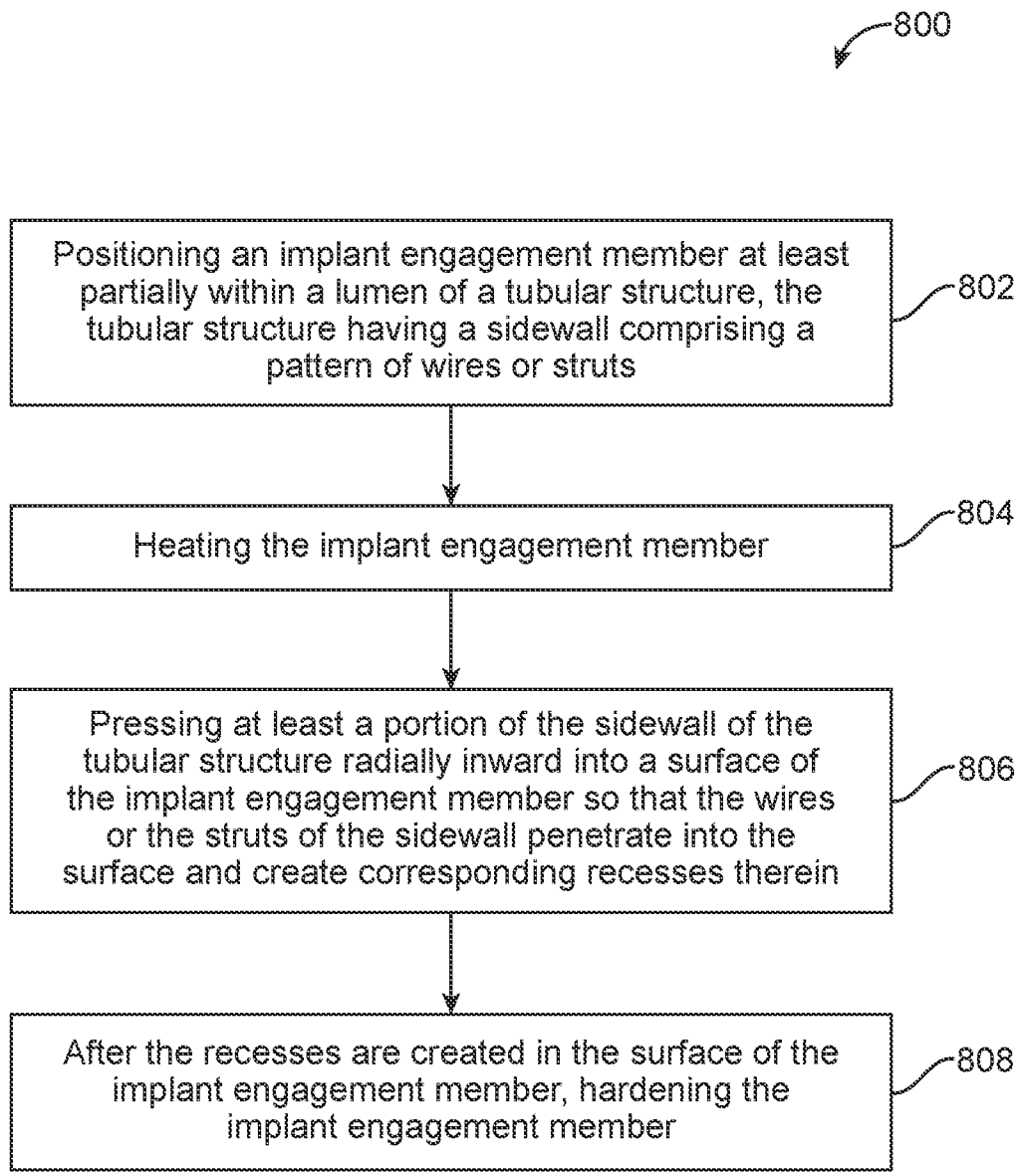
FIG. 8 illustrates a method of making a medical device in accordance with some embodiments.

FIG. 8 illustrates a method 800 of making a medical device in accordance with some embodiments. In the illustrated embodiments, the medical device has an elongated structure and an implant engagement member coupled to a distal end portion of the elongated structure. The medical device may optionally further include a sheath surrounding the implant engagement member and the elongated structure, and/or a handle coupled to a proximal end of the elongated structure. In some embodiments, the medical device may be the device 100 of FIG. 1, or any components or combination of components of the device 100. The method 800 includes: positioning an implant engagement member at least partially within a lumen of a tubular structure, the tubular structure having a sidewall comprising a pattern of wires or struts (item 802); heating the implant engagement member (item 804); pressing at least a portion of the sidewall of the tubular structure radially inward into a surface of the implant engagement member so that the wires or the struts of the sidewall penetrate into the surface and create corresponding recesses therein (item 806); and after the recesses are created in the surface of the implant engagement member, hardening the implant engagement member (item 808). The hardening of the object may be achieved by providing cooling treatment, chemical treatment, laser treatment, or passage of time.

Optionally, in the method 800, the implant engagement member is positioned within the lumen of a tubular structure prior to heating the implant engagement member.

Optionally, in the method 800, the implant engagement member is attached to a distal end portion of an elongated core member prior to being positioned within the lumen of the tubular structure.

Optionally, in the method 800, the wires or the struts of the tubular structure are pressed into the surface of the implant engagement member by axially stretching the tubular structure.

Optionally, in the method 800, the implant engagement member is hardened while the wires or struts of the tubular structure remain at least partially seated in the recesses formed in the surface of the implant engagement member.

Optionally, in the method 800, the recesses formed in the surface of the implant engaging member comprise a substantially mirror image of the pattern of wires or struts of the at least a portion of the tubular structure.

Optionally, in the method 800, the implant engagement member is hardened to a hardness that is at least 25 A.

Optionally, in the method 800, the tubular structure is the implant, and wherein the wires or the struts comprise braided wires.

Optionally, in the method 800, the tubular structure is the implant, and wherein the wires or the struts comprise struts formed by laser-cutting a tube.

Optionally, in the method 800, the tubular structure is a separate structure from the implant, and wherein the pattern of the wires or the struts is substantially identical to a pattern of wires or struts of the implant.

Optionally, the method 800 further includes separating the tubular structure from the implant engagement member prior to hardening the implant engagement member.

Optionally, the method 800 further includes separating the tubular structure from the implant engagement member, and positing at least a portion of the implant onto the implant engagement member such that the wires or the struts of the at least a portion of the implant are seated in respective recesses formed in the surface of the implant engagement member.

Optionally, in the method 800, the implant engagement member is heated using a sterilization heat source.

Optionally, in the method 800, at least one of the recesses comprises a groove forming a non-zero degree angle with respect to an imaginary line that is parallel to a longitudinal axis of the implant engagement member.

Optionally, in the method 800, the act of heating is performed before or after the act of pressing.

Optionally, the method 800 further includes placing the implant engagement member and the tubular structure in an introducer sheath to form at least a part of a product, and wherein the act of heating is performed on the at least a part of the product.

Optionally, in the method 800, the tubular structure is an implant which forms the recesses at the surface of the object, and is also configured to be delivered by the medical device.

Optionally, in the method 800, the medical device is configured to deliver an implant, and wherein the tubular structure and the implant are separate devices.

Optionally, in the method 800, the tubular structure for forming the recesses at the surface of the implant engagement member may have a spiral pattern, a grid pattern, a zig-zag pattern, a user-defined pattern, a symmetric pattern, an asymmetric pattern, etc. In some embodiments, any of such patterns may correspond with at least a part of the pattern formed by the implant components of the implant.

Optionally, in the method 800, wherein the created recesses comprise respective geometries that correspond with respective components (parts) of an implant. In some embodiments, a component of the implant may be a strand of a braid of the implant. In other embodiments, a component of the implant may be a marker of the implant. In further embodiments, a component of the implant may be a strut of a stent. In further embodiments, the implant may be a stent having a plurality of markers (e.g., 3 markers) disposed circumferentially at an end of the stent. In such cases, the created recesses in the method have respective geometries that correspond with the markers. For example, one of the recesses may have a shape, size, and/or location, that correspond with a shape, size, and/or location of one of the markers of the stent.

In the above embodiments, the device 100 has been described as having the sheath 130, the implant engagement member 110 and the elongated structure 102. In other embodiments, the device 100 may not include all of these components. For example, in other embodiments, the device 100 may not include the sheath 130. In further embodiments, the device 100 may not include the elongated structure 102. Thus, the term "device" is not necessarily limited to a complete product, and may refer to part or parts of a product, or part or parts of a design.

In one or more embodiments described herein, the device 100 may optionally further include a layer disposed at an inner surface of the sheath 130. The layer may be made from Teflon, or any of other materials that provide a smooth and low-frictional surface for allowing the implant 140 to "glide" thereagainst. In some cases, the layer may be considered to be a part of the sheath 130.

Also, in one or more embodiments described herein, the device 100 may optionally further include a steerable mechanism for steering the distal end 132 of the sheath 130. For example, the device 100 may include one or more steering wires contained in the wall of the sheath 130. The distal end(s) of the steering wire(s) is coupled to the distal end 132 of the sheath 130. During use, the proximal end(s) of the steering wire(s) may be tensioned by a manual control located at the handle 120, to thereby bend the distal end 132 of the sheath 130. In some cases, if the device 100 has multiple steering wires, one or more of the steering wires may be selectively tensioned to steer the distal end 132 of the sheath 130 in a desired direction. The steerability of the sheath 130 allows the distal end 132 of the sheath 130 to be steered through curvilinear passageway(s), such as tortuous blood vessel(s), inside the patient in order to reach a target location. In other embodiments, the device 100 may not include any steering wire.

In addition, in some embodiments, at least one of the grooves 502 of the implant engagement member 110 may be configured to mate with at least a part of a marker of an implant. In particular, in some embodiments, the proximal end 144 of the implant 140 may include a marker. In such cases, when creating the grooves 502 on the implant engagement member 110, one of the grooves 502 may be created for accommodating at least a part of the marker of the implant 140.

The following items are exemplary features of embodiments described herein. Each item may be an embodiment itself or may be a part of an embodiment. One or more items described below may be combined with other item(s) in an embodiment.

Item 1: A method of assembling an apparatus for delivering an implant to a deployment site in a patient's vasculature, includes: positioning an implant engagement member at least partially within a lumen of a tubular structure, the tubular structure having a sidewall comprising a pattern of wires or struts; heating the implant engagement member; pressing at least a portion of the sidewall of the tubular structure radially inward into a surface of the implant engagement member so that the wires or the struts of the sidewall penetrate into the surface and create corresponding recesses therein; and after the recesses are created in the surface of the implant engagement member, hardening the implant engagement member.

Item 2: In the method, the implant engagement member is positioned within the lumen of a tubular structure prior to heating the implant engagement member.

Item 3: In the method, the implant engagement member is attached to a distal end portion of an elongated core member prior to being positioned within the lumen of the tubular structure.

Item 4: In the method, the wires or the struts of the tubular structure are pressed into the surface of the implant engagement member by axially stretching the tubular structure.

Item 5: In the method, the implant engagement member is hardened while the wires or struts of the tubular structure remain at least partially seated in the recesses formed in the surface of the implant engagement member.

Item 6: In the method, the recesses formed in the surface of the implant engaging member comprise a substantially mirror image of the pattern of wires or struts of the at least a portion of the tubular structure.

Item 7: In the method, the implant engagement member is hardened to a hardness that is at least 25 A.

Item 8: In the method, the tubular structure is the implant, and wherein the wires or the struts comprise braided wires.

Item 9: In the method, the tubular structure is the implant, and wherein the wires or the struts comprise struts formed by laser-cutting a tube.

Item 10: In the method, the tubular structure is a separate structure from the implant, and wherein the pattern of the wires or the struts is substantially identical to a pattern of wires or struts of the implant.

Item 11: The method further includes separating the tubular structure from the implant engagement member prior to hardening the implant engagement member.

Item 12: In the method, the method further includes separating the tubular structure from the implant engagement member, and positing at least a portion of the implant onto the implant engagement member such that the wires or the struts of the at least a portion of the implant are seated in respective recesses formed in the surface of the implant engagement member.

Item 13: In the method, the implant engagement member is heated using a sterilization heat source.

Item 14: In the method, at least one of the recesses comprises a groove forming a non-zero degree angle with respect to an imaginary line that is parallel to a longitudinal axis of the implant engagement member.

Item 15: In the method, the act of heating is performed before the act of pressing.

Item 16: In the method, the act of heating is performed after the act of pressing.

Item 17: The method further includes placing the implant engagement member and the tubular structure in an introducer sheath to form at least a part of a product, and wherein the act of heating is performed on the at least a part of the product.

Item 18: A system for delivering an implant to a deployment site within a patient's vasculature, the tubular implant having a sidewall comprising a pattern of wires or struts, includes: an elongated core member; and an implant engagement member coupled to a distal end portion of the elongated core member, the implant engagement member comprising a surface having a plurality of recesses formed therein that receive and accommodate the wires or the struts of a corresponding sidewall portion of the tubular implant, wherein the recesses formed in the surface of the implant engagement member comprise a substantially mirror image of the pattern of the wires or the struts of the corresponding sidewall portion of the tubular implant.

Item 19: In the system, the wires or the struts of the tubular implant comprise braided wires.

Item 20: In the system, the wires or the struts of the tubular implant comprise struts formed by laser-cutting a tube.

Item 21: In the system, the implant engagement member has a hardness that is at least 25 A.

Item 22: The system further includes an additional recess in the surface of the implant engagement member configured to accommodate at least a portion of a marker of the tubular implant.

Item 23: The system further includes a delivery catheter; wherein the elongated core member, the implant engagement member, and the tubular implant are at least partially disposed within a lumen of, and slidable relative to, the delivery catheter; wherein the implant engagement member and the delivery catheter are configured to cooperate with each other to grip the tubular implant as the elongated core member is moved through and within the lumen of the delivery catheter; and wherein the tubular implant is configured to change from a compressed delivery configuration to an expanded deployed configuration with an expansion force that is sufficiently larger than a frictional force exerted by the recesses on the wires or the struts of the implant engagement member once the tubular implant is no longer confined within the delivery catheter.

Item 24: A medical device for delivering an implant, includes: an elongated structure having a distal end and a proximal end; and an implant engagement member coupled to the distal end of the elongated structure; wherein the implant engagement member comprises a surface having a plurality of grooves, wherein the grooves form a pattern that matches at least a part of a braid pattern of the implant.

Item 25: In the medical device, at least one of the grooves form an angle that is larger than 0 degree with respect to an imaginary line that is parallel to a longitudinal axis of the elongated structure.

Item 26: In the medical device, the pattern of the grooves of the implant engagement member comprises a crisscross pattern.

Item 27: In the medical device, the implant engagement member has a hardness that is at least 25 A.

Item 28: In the medical device, the implant engagement member is configured to engage with an inner surface of the implant while the grooves accommodate braid elements of the implant.

Item 29: In the medical device, one of the grooves of the implant engagement member is configured to accommodate at least a part of an implant marker.

Item 30: In the medical device, the grooves comprise permanent indentations.

Item 31: In the medical device, the implant comprises a tubular structure with an external cross-sectional dimension, and wherein a cross-sectional dimension of the implant engagement member is less than the external cross-sectional dimension of the tubular structure.

Item 32: The medical device further includes a sheath with a lumen, wherein the implant engagement member is disposed in the lumen of the sheath.

Item 33: In the medical device, the implant engagement member and the sheath are configured to cooperate with each other to grip and to release the implant.

Item 34: The medical device further includes the implant, wherein the implant has a delivery configuration when confined in the lumen of the sheath, and a deployed configuration when outside the lumen of the sheath.

Item 35: In the medical device, the implant is configured to change from the delivery configuration to the deployed configuration with an expansion force that is larger than a frictional force exerted by the grooves on the implant.

Item 36: In the medical device, the expansion force is larger than the gripping force by a sufficient amount that allows the implant to immediately spring open to assume the deployed configuration when the implant is unconfined by the sheath.

Item 37: A method of making a medical device, the medical device having an elongated structure and an implant engagement member coupled to a distal end portion of the elongated structure, includes: holding an object to be formed as the implant engagement member; placing a tubular structure over the object, or inserting the object into the tubular structure, wherein the tubular structure has a braid pattern; pressing the tubular structure radially inward toward the object to create grooves at a surface of the object, wherein the created grooves form a pattern that matches at least a part of the braid pattern of the tubular structure; and hardening the object after the grooves are created at the surface of the object.

Item 38: In the method, the tubular structure is an implant.

Item 39: In the method, the implant is for forming the grooves at the surface of the object, and is also configured to be delivered by the medical device.

Item 40: In the method, the medical device is configured to deliver an implant, and wherein the tubular structure and the implant are separate devices.

Item 41: In the method, the object has a hardness that is at least 25 A.

Item 42: The method further includes heating the object using a sterilization heat source or a separate heat source that is different from the sterilization heat source.

Item 43: A system for making a medical device, the medical device having an elongated structure and an implant engagement member coupled to a distal end portion of the elongated structure, includes: an object to be formed as the implant engagement member; and a tubular structure with a braid pattern, wherein the tubular structure is configured to press against the object to create grooves at the surface of the object, wherein the grooves form a pattern that corresponds with the braid pattern of the tubular structure.

Item 44: In the system, the tubular structure is an implant.

Item 45: In the system, the tubular structure is different from an implant.

As used in this specification, the term "surface" may refer to a real surface or an imaginary surface, wherein the real/imaginary surface may be a curvilinear surface or a rectilinear surface. Also, the term "surface" is not limited to any continuous curvilinear or rectilinear planar item, and may refer to any item having points that define the surface or that lie with the surface.

Also, as used in this specification, the term "recess" may refer to an indentation or a depression on a surface formed by indenting or depressing a part of the surface, or may refer to an indentation or depression on a surface formed by any of other techniques, including but not limited to molding, 3D printing, etc. For example, an object may be formed to have the recess using a mold, or the object with the recess may be created by 3D printing. Also, the term "recess" may refer to an elongated indentation or depression, such as a groove (e.g., a channel), or may refer to an indentation or depression having any size and/or shape.

In addition, as used in this specification, the terms "apparatus", "device", "system" may refer to a product, one or more component(s), a part of a product, or a part of a component. In some cases, any of these terms may refer to two or more components that are coupled to each other, and/or that have functional and/or positional relationship with respect to each other. Also, in some cases, these terms are synonymous to each other.

Furthermore, as used in this specification, the term "distal end" of an item (e.g., elongated structure, elongated core member, etc.) may refer to any part of such item that is within ⅓ of a total length of the item measured from a distal tip of the item. Similarly, the term "proximal end" of an item (e.g., elongated structure, elongated core member, etc.) may refer to any part of such item that is within ⅓ of a total length of the item measured from a proximal tip of the item. The term "distal end portion" of an item may refer to any part of the distal end of the item.

Although particular embodiments have been shown and described, it will be understood that it is not intended to limit the claimed inventions to the preferred embodiments, and it will be obvious to those skilled in the art that various changes and modifications may be made without department from the scope of the claimed inventions. The specification and drawings are, accordingly, to be regarded in an illustrative rather than restrictive sense. The claimed inventions are intended to cover alternatives, modifications, and equivalents.

The invention claimed is:

1. A method of making an apparatus for delivering an implant to a deployment site in a patient's vasculature, the method comprising:
positioning an implant engagement member at least partially within a lumen of a tubular structure, the tubular structure having wires forming a pattern, the implant engagement member having a surface that is in a first state;
creating a first set of first recesses at the surface of the implant engagement member using respective tabs of the tubular structure; and
creating a second set of second recesses at the surface of the implant engagement member using parts of the wires of the tubular structure, wherein the surface of the implant engagement member is in a second state after the first recesses and the second recesses are created;
wherein each of the first recesses is configured to receive an entirety of a corresponding one of the tabs of the tubular structure;
wherein the parts of the wires comprise a first wire part and a second wire part, the first wire part and the second wire part defining a space therebetween; and
wherein after the second recesses are created, the first wire part, the second wire part, and the space between the first wire part and the second wire part, are in one of the second recesses.

2. The method of claim 1, wherein the implant engagement member is a distal-most part of a pusher configured to advance the implant.

3. The method of claim 2, wherein the implant engagement member is configured to transfer a majority of a force applied at a proximal end of the pusher to a proximal end of the implant.

4. The method of claim 3, wherein the implant engagement member is configured to push only a proximal end of the implant to advance the implant distally while an entirety of the implant is inside a catheter.

5. The method of claim 3, wherein the tubular structure is the implant.

6. The method of claim 1, wherein at least a part of the one of the second recesses has a tapered configuration.

7. The method of claim 6, wherein opposing sides of the tapered configuration are formed respectively by the first and second wire parts.

8. The method of claim 6, wherein the at least the part of the one of the second recesses extends continuously across an area between opposing tapering sides of the tapered configuration.

9. The method of claim 1, wherein the first recesses formed at the surface of the implant engaging member comprise a substantially mirror image of the tabs of the tubular structure.

10. The method of claim 1, wherein the implant engagement member is hardened to a hardness that is at least 25 A.

11. The method of claim 1, wherein the tubular structure is the implant, and wherein the wires comprise braided wires of the implant.

12. The method of claim 1, wherein the tubular structure is the implant, and wherein the wires are formed by laser-cutting a tube to form the tubular structure.

13. The method of claim 1, wherein the tubular structure is a separate structure from the implant.

14. The method of claim 13, further comprising separating the tubular structure from the implant engagement member prior to hardening the implant engagement member.

15. The method of claim 13, further comprising separating the tubular structure from the implant engagement member, and positioning at least a portion of the implant onto the implant engagement member such that parts of the wires of the implant are seated in the second recesses formed at the surface of the implant engagement member.

16. The method of claim 1, further comprising heating the implant engagement member using a sterilization heat source.

17. The method of claim 1, further comprising placing the implant engagement member and the tubular structure in an introducer sheath.

18. The method of claim 1, wherein the acts of creating the first and second recesses are achieved by moving the tabs and the parts of the wires radially inward.

19. The method of claim 18, wherein the act of moving the tabs and the parts of the wires is achieved by stretching the tubular structure.

20. The method of claim 1, wherein the implant engagement member is hardened while the parts of the wires of the tubular structure remain at least partially seated in the second recesses formed at the surface of the implant engagement member.

21. The method of claim 1, further comprising placing the implant and the implant engagement member in a catheter.

\* \* \* \* \*